United States Patent
Bruesehaber et al.

(10) Patent No.: US 10,004,383 B2
(45) Date of Patent: Jun. 26, 2018

(54) METHOD FOR CONNECTING AT LEAST TWO COMPONENTS OF AN ENDOSCOPE, COMPONENTS OF AN ENDOSCOPE AND ENDOSCOPE

(71) Applicant: KARL STORZ GmbH & Co. KG, Tuttlingen (DE)

(72) Inventors: Steffen Bruesehaber, Mahlstetten (DE); Andreas Deutschendorf, Spaichingen (DE); Siegfried Hoefig, Muehlheim (DE); Bernd Krause, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 29 days.

(21) Appl. No.: 15/088,414

(22) Filed: Apr. 1, 2016

(65) Prior Publication Data
US 2016/0287052 A1 Oct. 6, 2016

(30) Foreign Application Priority Data

Apr. 1, 2015 (DE) .................. 10 2015 105 069

(51) Int. Cl.
*B23K 31/02* (2006.01)
*A61B 1/00* (2006.01)
(Continued)

(52) U.S. Cl.
CPC ........ *A61B 1/0011* (2013.01); *A61B 1/00128* (2013.01); *B23K 1/0008* (2013.01);
(Continued)

(58) Field of Classification Search
CPC ..... A61B 1/0011; A61B 1/00128; B23K 3/06; B23K 1/18; B23K 35/0244;
(Continued)

(56) References Cited

U.S. PATENT DOCUMENTS 1,889,974 A * 12/1932 Chamberlain ........... B23K 1/20
228/135
2,014,612 A * 9/1935 Borton ..................... B23K 1/20
148/220
(Continued)

FOREIGN PATENT DOCUMENTS

CN 103386525 A * 11/2013
DE 2 117 629 A1 11/1971
(Continued)

OTHER PUBLICATIONS

Machine translation of CN 103386525 A (no date available).*
(Continued)

*Primary Examiner* — Kiley Stoner
(74) *Attorney, Agent, or Firm* — Muncy, Geissler, Olds & Lowe, P.C.

(57) ABSTRACT

In the case of a method according to the invention for connecting at least two components of an endoscope, at least one brazing preform, which contains a high-temperature brazing solder, is introduced into at least one brazing solder reservoir of at least one of the components, the at least two components are held in relation to one another in such a way that at least one brazing gap that is in capillary connection with the at least one brazing solder reservoir is formed between joining regions of the at least two components that are assigned to one another, and the arrangement (1, 22) comprising the at least two components and the at least one brazing preform is heated to a brazing temperature of the high-temperature brazing solder. The invention also relates to a component of an endoscope and to an endoscope.

10 Claims, 4 Drawing Sheets

(51) Int. Cl.
- *B23K 1/00* (2006.01)
- *B23K 35/02* (2006.01)
- *B23K 35/30* (2006.01)
- *B23K 1/18* (2006.01)
- *B23K 3/06* (2006.01)

(52) U.S. Cl.
CPC .................. *B23K 1/18* (2013.01); *B23K 3/06* (2013.01); *B23K 35/0233* (2013.01); *B23K 35/0244* (2013.01); *B23K 35/3033* (2013.01)

(58) Field of Classification Search
CPC .............. B23K 35/0233; B23K 1/0008; B23K 35/3033; B23K 1/00–1/206; B23K 3/0623
USPC .................. 228/135–140, 56.3, 245–262
See application file for complete search history.

(56) References Cited

U.S. PATENT DOCUMENTS

| | | | | |
|---|---|---|---|---|
| 2,050,728 A * | 8/1936 | Ost | ........................ | F16L 13/08 174/21 R |
| 2,553,836 A * | 5/1951 | Stone | .................... | E21B 17/042 285/115 |
| 3,078,551 A * | 2/1963 | Patriarca | ................ | B21D 39/06 228/134 |
| 3,198,556 A * | 8/1965 | Kruse | ..................... | F16L 13/08 285/289.1 |
| 3,327,892 A * | 6/1967 | Lloyd | ..................... | B23K 1/20 220/612 |
| 3,464,617 A * | 9/1969 | Pescatrice | ................ | B23K 1/20 228/245 |
| 3,667,109 A * | 6/1972 | Alcenius | .................. | B23K 1/20 228/133 |
| 3,775,836 A * | 12/1973 | Jackson | ................... | B23K 1/18 228/168 |
| 3,906,616 A * | 9/1975 | Bryand | ................ | B23K 1/0014 228/170 |
| 3,968,982 A * | 7/1976 | Belicic | .................... | F16B 4/006 228/56.3 |
| 4,448,343 A * | 5/1984 | Kochka | .................. | B23K 1/203 138/98 |
| 4,477,012 A * | 10/1984 | Holland | ............... | B23K 1/0014 228/181 |
| 4,572,938 A * | 2/1986 | Driggers | .................. | B23K 1/18 219/552 |
| 4,576,325 A * | 3/1986 | Maurice | .................. | B23P 11/00 188/26 |
| 4,620,662 A * | 11/1986 | Driggers | .............. | B23K 1/0012 228/126 |
| 4,624,866 A * | 11/1986 | Cheng | ..................... | B23K 1/20 138/98 |
| 4,650,110 A * | 3/1987 | Cheng | ..................... | B21D 39/04 138/98 |
| 5,267,684 A * | 12/1993 | Catheline | ................. | B23K 1/18 174/152 GM |
| 5,333,918 A * | 8/1994 | Crout | ..................... | F16L 13/08 228/136 |
| 5,536,244 A | 7/1996 | Müller et al. | | |
| 5,557,837 A * | 9/1996 | Thiard-Laforet | ...... | H02K 3/505 228/165 |
| 5,659,944 A * | 8/1997 | Thiard-Laforet | ...... | H02K 3/505 228/165 |
| 5,709,337 A * | 1/1998 | Moser | ................. | G01L 19/0084 228/124.6 |
| 5,839,644 A * | 11/1998 | Windle | .................... | B21C 37/28 228/168 |
| 6,250,535 B1 * | 6/2001 | Sollami | ................ | B23K 1/0008 228/125 |
| 6,574,864 B1 * | 6/2003 | Meissner | ............. | H01H 33/664 228/258 |
| 7,451,908 B2 * | 11/2008 | Gropallo | .............. | B23K 1/0012 228/183 |
| 7,926,178 B2 * | 4/2011 | Thomson | ................ | F23D 11/36 228/135 |
| 2005/0077343 A1 | 4/2005 | Sato et al. | | |
| 2006/0254047 A1 * | 11/2006 | Stroebel | ............... | B23K 1/0008 29/623.2 |
| 2008/0277455 A1 * | 11/2008 | Hoffmann | ............ | B23K 1/0012 228/183 |
| 2009/0200363 A1 * | 8/2009 | Means | ................. | B23K 1/0012 228/246 |
| 2010/0126018 A1 * | 5/2010 | Headley | ............... | B23K 1/0018 29/889.22 |
| 2010/0264134 A1 * | 10/2010 | Peterson | ................ | B23K 1/002 219/675 |
| 2011/0111247 A1 * | 5/2011 | Lemke | ................. | B23K 1/0008 428/600 |
| 2012/0123210 A1 | 5/2012 | Eisenkolb et al. | | |
| 2013/0043760 A1 * | 2/2013 | Osborne | ............ | H02K 15/0012 310/211 |
| 2014/0008416 A1 * | 1/2014 | Visser | ..................... | B23P 13/04 228/56.3 |
| 2014/0008417 A1 * | 1/2014 | Visser | ..................... | B23K 35/0222 228/56.3 |
| 2015/0165218 A1 * | 6/2015 | Markham | ............ | A61N 1/3754 607/116 |
| 2017/0008130 A1 * | 1/2017 | Miklos | ....................... | B22F 3/17 |
| 2017/0036306 A1 * | 2/2017 | Campbell | .......... | B23K 35/0222 |
| 2017/0203106 A1 * | 7/2017 | Markham | ............ | A61N 1/3754 |

FOREIGN PATENT DOCUMENTS

| | | | | |
|---|---|---|---|---|
| DE | 2117629 A1 * | 11/1971 | ............. | B23K 1/20 |
| DE | 2555960 B1 * | 2/1977 | .......... | B23K 1/0008 |
| DE | 93 09 545 U1 | 8/1993 | | |
| DE | 19606257 A1 * | 8/1996 | ............... | B23K 1/19 |
| DE | 10 2010 050 513 A1 | 5/2012 | | |
| FR | 2276528 A1 * | 1/1976 | ............... | B23K 1/20 |
| FR | 2333607 A1 * | 7/1977 | ............... | B23K 1/20 |
| GB | 1497084 A * | 1/1978 | ............ | H01R 4/022 |
| JP | 58084671 A * | 5/1983 | ............... | B23K 1/18 |
| JP | 07155937 A * | 6/1995 | ........... | B23K 1/0008 |
| WO | WO 2007/070989 A1 | 6/2007 | | |

OTHER PUBLICATIONS

Dorn et al., Hartlöten und Hochtemperaturlöten Grundlagen und Anwendung, Renningen: expert verlag, pp. 50-63 and 123-128 (2007) including English Abstract.

* cited by examiner

METHOD FOR CONNECTING AT LEAST TWO COMPONENTS OF AN ENDOSCOPE, COMPONENTS OF AN ENDOSCOPE AND ENDOSCOPE

This nonprovisional application claims priority under 35 U.S.C. § 119(a) to German Patent Application No. 10 2015 105 069.2, which was filed in Germany on Apr. 1, 2015, and which is herein incorporated by reference.

BACKGROUND OF THE INVENTION

Field of the Invention

The present invention relates to a method for connecting at least two components of an endoscope or medical instrument, to a component of an endoscope that is designed for connecting to at least one further component of the endoscope by means of high-temperature brazing and for this purpose has a joining region, and to an endoscope with an endoscope head, which has a housing and at least one built-in part and/or at least one built-on part.

Description of the Background Art

Endoscopes are used for many applications in medicine and technology. An endoscope typically comprises an elongate shank, which is suitable for inserting into a cavity, for instance into a cavity inside the body or a cavity in a technical article, and in the distal end region of which, i.e. remote from the user, there is arranged an endoscope objective lens for producing an endoscopic image of an object field located in the cavity. The shank may be of a rigid, semirigid or flexible design. The recorded endoscopic image is typically passed on to the proximal end of the endoscope, i.e. near the user, by way of an image retransmitter arranged within the shank. Known to act as image retransmitters are in particular lens systems, which may comprise a plurality of rod lenses, and ordered bundles of optical fibers. Since sufficient light is not generally available in the cavity, a light guiding system having optical fibers is also usually arranged within the shank of the endoscope, in order to transport light to the distal end of the endoscope for illuminating the object field. Furthermore, the shank may have one or more working channels for leading through endoscopic working instruments, with which manipulations can be carried out within the cavity. Also often provided within the shank are flushing, suction and insufflation channels, with which liquids or gases can be transported into the cavity and out from it during endoscopic operations.

Generally arranged at the proximal end of the shank is an endoscope head, which remains outside the cavity during the use of the endoscope. The endoscope head has a housing and a plurality of built-in parts and built-on parts. In particular, the endoscope head is adjoined on the distal side by the shank of the endoscope, on the proximal side by an eyepiece cup or a connection for an endoscopic video camera, and on the side of the endoscope head there is a connection for connecting a fiber optic cable, with which the illuminating light can be supplied from an external light source. Furthermore, the endoscope head may have flushing, suction and insufflation connections and also inlets of working channels, through which endoscopic working instruments can be inserted, as well as guides for the channels and optical elements arranged within the endoscope head. Typically, at least the housing of the endoscope head can be formed of high-grade steel.

During the use and the preparation of an endoscope, it is exposed to considerable mechanical, thermal and chemical loads. In particular, vibrations may act on the endoscope, considerable forces may be exerted on the connections during use, and the endoscope is exposed to chemically aggressive media and to increased pressure and increased temperature during cleaning and sterilization. It is therefore necessary to connect the built-in parts and built-on parts to the housing of the endoscope and to one another securely and reliably and in a sealed and thermally stable manner.

For this purpose it is known to connect the components of the endoscope head to one another by laser welding. However, the melting of the material during the laser welding has the effect of weakening the component concerned in the region of the welded connection, which in particular in the case of thin-walled components, which are used in the case of endoscopes with a small shank diameter, impairs the strength. In addition, laser welding does not always successfully produce a fluid-tight connection, in particular in the case of relatively long weld seams. To increase the strength and to ensure the seal-tightness of a laser-welded connection, it is often additionally secured by adhesion. Since in the production of an endoscope or an endoscope head a plurality of connections have to be created between components, which moreover are often arranged within the housing of the endoscope head, and are therefore only poorly accessible, a large number of successive production steps are necessary, which further increases the production costs.

US 2005/0077343 A1 discloses a method for brazing two or more high-grade steel components of a medical endoscope, wherein one component is connected to another by means of a brazing solder material that contains at least 62.5% by weight of gold. In this case, the components are subjected in a first step to a heat treatment at a temperature of 1050 to 1200° C. in a hydrogen-containing atmosphere or in a vacuum. In a second step, one of the components may form a gap with the other, and in a third step the brazing solder material is fed to the gap in a molten state in order to connect the components to one another. For feeding in the brazing solder material, it may be wound as a wire around a tube to be brazed in, for example, or else be applied as a paste in the region of the connection. However, this known method is not optimal in terms of costs and suitability for use, in particular in the production of an endoscope head.

SUMMARY OF THE INVENTION

The object of the present invention is to provide a method for connecting at least two components of an endoscope, wherein the aforementioned disadvantages are avoided as far as possible. The object of the present invention is also to provide a component of an endoscope that is suitable for such a method and also a corresponding endoscope.

A method according to the invention serves for connecting at least two components of an endoscope. In particular, the method serves for permanently connecting the at least two components with a material bond, i.e. joining them. The components are preferably metallic components, in particular components of high-grade steel; however, the components may also at least partially be formed for instance of titanium, of a titanium alloy or of some other material, preferably metallic material, that is suitable for use in an endoscope and for connection by means of high-temperature brazing.

The endoscope comprises in particular an elongate rigid or semirigid shank, which is suitable for inserting into a cavity and receives an illuminating optical system, for passing on illuminating light from a proximal end region of the endoscope to the distal end region for illuminating an object field to be observed within the cavity, and an observing optical system, for recording an image of the object field and for passing on the image to the proximal end region of the endoscope. Connected to the shank in the proximal end region of the endoscope is an endoscope head, which has in particular a light connection for connecting an optical cable of an external illuminating light source. On the endoscope head there may also be provided an eyepiece for the visual viewing of the endoscopic image passed on from the distal end and/or a connection for an endoscopic video camera. Furthermore, operator control elements and also the mouths of one or more working, insufflation, suction and/or flushing channels may be arranged at the endoscope head. Such an endoscope is also referred to as an "endoscope optical system". The endoscope may be an endoscope for medical applications, i.e. for viewing a cavity within a human or animal body, or else a technical endoscope, which is intended for non-medical applications. The method according to the invention serves in particular for connecting at least two components of the endoscope head, for example a housing of the endoscope head to a built-in part to be inserted into it or to a built-on part to be attached to it and/or for connecting a built-in part to another built-in part or a built-on part.

According to the invention, in a first method step at least one brazing preform, which contains a high-temperature brazing solder, is introduced into at least one brazing solder reservoir of at least one of the components to be connected to one another. The at least one brazing preform contains the high-temperature brazing solder for example as metal powder, which is mixed with a binder and forms a solid or moldable brazing solder material; the high-temperature brazing solder is consequently introduced into the at least one brazing solder reservoir in the solid state of aggregation. The at least one brazing solder reservoir may be formed for example as a pocket or cavity of one of the at least two components, into which the at least one brazing preform is introduced. The brazing preform is preferably preformed in such a way that it can be easily introduced into the brazing solder reservoir, for instance can be pushed in, and substantially fills the reservoir.

In a second method step, the at least two components to be connected to one another are arranged and held in relation to one another in such a way that at least one brazing gap is formed between joining regions of the at least two components that are assigned to one another. The joining regions are regions corresponding to one another of the surfaces of the components that are arranged such that they are in particular opposite one another at a small distance and thereby form a brazing gap. The joining regions respectively assigned to one another of the at least two components form a joining location. The brazing gap is in capillary connection with the at least one brazing solder reservoir, i.e. the construction of the brazing solder reservoir and the arrangement of the components in relation to one another is such that, after melting, the liquid solder can be drawn out of the brazing solder reservoir into the brazing gap by capillary forces, in order to completely or partially fill this gap. For example, the at least one brazing solder reservoir may have an opening that opens out into the brazing gap or is in connection with it directly or is in connection with the brazing gap by way of a capillary or a gap that corresponds in its width substantially to the brazing gap. The opening of the brazing solder reservoir may be the same as that through which the brazing preform has been introduced into the brazing solder reservoir. In the second step of the method according to the invention, the high-temperature brazing solder is contained in the at least one brazing preform while still in a solid form.

The second method step may be performed at the same time as the first-mentioned first method step or, depending on the type and construction of the components to be connected to one another and depending on the accessibility of the at least one brazing solder reservoir, may also take place before the aforementioned first step. Thus, it may be provided for example that the at least one brazing solder reservoir is only created by the arrangement of the at least two components, and the at least one brazing preform is only introduced into the at least one brazing solder reservoir after the components have been arranged in relation to one another.

Furthermore, according to the invention, in a third method step, the arrangement, created by the first method step and the second method step, possibly by carrying out the first method step and the second method step for a number of joining locations and comprising the at least two components to be connected to one another, including the at least one brazing preform introduced in the at least one brazing solder reservoir, is heated to a brazing temperature of the high-temperature brazing solder, i.e. in particular to a temperature that corresponds at least to the melting temperature of the high-temperature brazing solder. The heating may be carried out for instance in a furnace, which may for example be a continuous furnace; in this case, the heating may take place in a known way under shielding gas or in a vacuum, whereby tarnishing of the surface and slag formation can be avoided. Heating to the brazing temperature has the effect that the high-temperature brazing solder is liquefied, after which it is drawn out of the brazing solder reservoir into the at least one brazing gap by capillary forces and completely or partially fills the gap. Once the solder has filled the at least one brazing gap, the arrangement is left to cool down until the high-temperature brazing solder has solidified and the at least two components have been connected to one another by the brazed connection.

The method according to the invention may comprise further steps, for instance a pretreatment of the components to be connected to one another or the joining regions, in order to facilitate the flowing of the liquefied solder into the at least one brazing gap. Further method steps, which may in particular concern the production of the components, the at least one brazing preform and the assembly and adjustment of the endoscope, may also be provided before, between or after the aforementioned three method steps in the course of the production of the endoscope.

The fact that the high-temperature brazing solder is provided as at least one brazing preform which is introduced into at least one brazing solder reservoir of at least one of the components to be connected to one another means that it is made possible for brazed connections that are seal-tight and can withstand high loads can be easily created, even in the case of complex geometries of the components connected to one another. At the same time, greater stability of the joining locations and also an increase in quality with regard to the seal-tightness can be achieved in particular by a connecting area that is larger in comparison with laser welding, and also by no material of the components to be connected being melted. Furthermore, simplification of the production process is made possible, generally obviating the need for additional fixing or sealing of the joining locations by means of adhesive. It is often possible when connecting the at least two components of the endoscope or when producing an endoscope head by the method according to the invention to dispense largely or entirely with laser welding, whereby the runthrough time in production can be reduced and the production costs can be lowered. Furthermore, manual feeding of the brazing solder is not necessary, as a result of which the production process can likewise be simplified, and what is more an always constant amount of brazing solder can be ensured. Similarly, the components to be connected to one another can themselves be of a structurally simpler design, since no special measures are necessary for making laser welding possible on internal components; what is more, a weight saving may be achievable as a result.

According to a preferred embodiment of the invention, for forming the at least one brazing gap, the at least two components are held in relation to one another, at least on the basis of the previously described second method step, by the components being held against one another with interlocking, frictional or material-bonding engagement. The two components to be connected to one another may for example be fastened to one another by a thread or by individual laser welding points and thereby held in such a way that the at least one brazing gap is created and sustained during the further method steps, in particular the third method step. This may make it possible to dispense with an auxiliary device for joining the at least two components. As a result, the production of the endoscope can be further simplified.

In an advantageous way, the at least two components to be connected to one another may have a plurality of joining locations, to which at least one brazing solder reservoir is respectively assigned. Preferably, each joining location is assigned precisely one brazing solder reservoir. The joining locations may be respectively formed by a joining region of a first component and a joining region assigned thereto of a second component that is to be connected to the first, the number of joining locations preferably not being contiguous with one another but formed separately. The fact that the at least two components to be connected to one another have a plurality of joining locations to which at least one brazing solder reservoir is respectively assigned means that a particularly reliable and secure connection of the at least two components is made possible. This applies in particular in the case where the components to be connected to one another have a complex geometry or the joining locations are poorly accessible. Furthermore, it is possible in particular according to the invention to connect a plurality of joining locations with the high-temperature brazing solder in a single heating step, whereby the production of an endoscope or an endoscope head can be further simplified.

More than two components are preferably connected to one another, at least two joining locations being provided. Here it is likewise possible to make use of the fact that a number of joining locations, in particular all of the joining locations, can be filled with high-temperature brazing solder simultaneously or in a single heating step. This allows the number of necessary production steps in the production of an endoscope or an endoscope head to be further reduced, and consequently production to be further simplified.

In the event that a number of joining locations are provided or more than two components are connected to one another, it may be provided in particular that the first method step and the second method step are carried out for a first joining location or for the connection of a first component to a second component, after that the first method step and the second method step are carried out for a second joining location or for the connection of the first component and/or the second component to a third component, and after that are possibly carried out for further joining locations or components. The sequence of the first method step and the second method step may be different for each joining location or each further component. The sequence of the method steps may in this case be chosen according to the type and construction of the components to be connected to one another and according to the accessibility of the brazing solder reservoirs concerned.

According to a particularly preferred embodiment of the invention, the high-temperature brazing solder is a nickel-based solder or iron-based solder. Such a nickel-based solder or else nickel solder contains a nickel fraction of for example approximately 75% and may contain further metallic and/or nonmetallic constituents. The brazing preform may additionally contain a binder, which evaporates during the heating step. When using a nickel-based solder, the brazing temperature lies for example in the range between 1050 and 1200° C. In particular when heating in a vacuum or under a shielding gas, a flux is generally not required, whereby flux inclusions can also be avoided and the corrosion tendency can be reduced. Use of a nickel-based solder allows a particularly secure connection of the at least two components to be achieved. Furthermore, as a result, discoloration of visible brazed seams during the sterilization necessary for medical endoscopes, in particular autoclaving, can be easily avoided. Nickel-based solder is particularly advantageous for connecting components of high-grade steel; for components of other materials, a different brazing solder material may be used, for instance titanium solder for connecting components of titanium.

The brazing preform is preferably produced from a brazing mat, for example by punching out from a sheet-like brazing mat. In this case, the brazing mat may have previously been rolled out to a suitable thickness. The brazing mat may contain the high-temperature brazing solder in powder form, and also a binder and possibly further constituents. As a result, the preparation of a brazing preform of the desired dimensions for filling the at least one brazing solder reservoir is made easily possible.

According to a preferred embodiment of the method according to the invention, after being introduced into the brazing solder reservoir concerned and before heating, the at least one brazing preform is fixed within the brazing solder reservoir. Such fixing may take place for example with interlocking or frictional engagement, for which the brazing solder reservoir is correspondingly shaped, for instance as a pocket, which is filled virtually completely by the brazing preform. The at least one brazing preform is preferably fixed in the respective brazing solder reservoir by adhesion. An adhesive used for this purpose may in particular comprise a solvent, which makes an uppermost layer of the brazing mat or the brazing preform begin to dissolve. As a result, the brazing preform is adhesively attached on the surface of the component concerned, i.e. on the inner surface of the brazing solder reservoir. It is thereby easily possible to achieve the effect that the brazing preform remains in place during further handling, up until the melting of the high-temperature brazing solder, and that the liquefied high-temperature brazing solder flows into the brazing gap assigned to the brazing solder reservoir. As a result, the handling of the components to be connected to one another is simplified, so that even a plurality of components can be easily connected to one another with a plurality of joining locations.

The brazing solder reservoir and the brazing preform are preferably at least dimensioned in such a way that the at least one brazing solder reservoir is substantially filled by the brazing preform introduced into it and during the heating the brazing gap assigned to the at least one brazing solder reservoir is substantially filled completely with the high-temperature brazing solder. In particular, the volume of the brazing solder reservoir may be at least equal to the volume to be filled of the brazing gap; the volume of the brazing solder reservoir is preferably made to be greater than the volume of the brazing gap by at least an amount that corresponds to the proportion of the binder in the brazing preform. In addition, an excess of brazing solder material beyond that and a correspondingly greater dimensioning of the brazing solder reservoir and the brazing preform may be provided. The excess may serve for example for ensuring complete filling of the brazing gap even when tolerances occur, and may possibly remain in the brazing solder reservoir after the melting. In particular, depending on the geometry of the joining location, an excess may be provided in order in addition to the filling of the brazing gap to form a fillet seam. The fact that the brazing solder reservoir and the brazing preform are dimensioned at least such that the brazing solder reservoir is filled by the brazing preform and furthermore the brazing gap is filled substantially completely with the high-temperature brazing solder means that a particularly reliable and seal-tight connection of the at least two components to be connected to one another can be achieved.

A component according to the invention of an endoscope, in particular the head of an endoscope, is designed for connecting to at least one further component of the endoscope or the endoscope head by means of high-temperature brazing, in particular for connecting to the at least one further component by means of the method according to the invention that is described above. For this purpose, the component according to the invention has a joining region, which is designed to form together with a corresponding joining region of the further component a joining location for the connection of the two components. According to the invention, the component has a brazing solder reservoir assigned to the joining region or the joining location. The brazing solder reservoir is designed to receive a brazing preform, which contains a high-temperature brazing solder and is arranged in such a way that the high-temperature brazing solder liquefied by heating can flow under the effect of brazing forces into a brazing gap that can be formed between the joining region of the component and a joining region of the further component and can at least partially fill this gap. The brazing solder reservoir is arranged in such a way that it is in capillary connection with a brazing gap that can be formed between the joining regions assigned to one another of the component and the at least one further component, for instance in that the brazing solder reservoir has an opening that opens out into the joining region of the component or is in connection with it by way of a capillary. The way in which the component of the endoscope is configured according to the invention makes it possible for a connection that is secure and seal-tight even in the case of relatively long brazed seams to be easily produced between the component according to the invention and the further component.

An endoscope according to the invention comprises an endoscope head and an elongate, preferably rigid or semi-rigid shank, in which an illuminating optical system and an observing optical system are received and which is connected to the endoscope head. The endoscope head has a housing and at least one built-in part and/or at least one built-on part, the at least one built-in part, the at least one built-on part and/or the housing being designed in the same way as the component described above. In particular, the housing and/or the at least one built-in part and/or the at least one built-on part have been connected to one another by means of high-temperature brazing solder and connected to one another by the method described above. The at least one built-in part may for example be an inner bush for receiving a proximal end portion of an optical tube for receiving the observing optical system and possibly a lightguide channel for receiving the light guides of the illuminating optical system. Further built-in parts may serve for example for holding optical components within the endoscope head and/or for guiding working, insufflation, suction and/or flushing channels. The at least one built-on part may for example be a sleeve of a light connection for connecting an optical cable of an external illuminating light source. Further built-on parts of the endoscope head may be for example the mouth of a working channel and insufflation, suction and/or flushing connections, as well as an outer shank of the endoscope. The fact that the at least one built-in part, the at least one built-on part and/or the housing are designed as described above, and consequently are designed for connecting by means of the method according to the invention that is described above, and in particular have been connected to one another by the method according to the invention, means that an endoscope is created with an endoscope head in which the at least one built-in part or the at least one built-on part are connected to the housing or to one another in a secure and hermetically seal-tight manner, and which can be produced in an easy and low-cost way.

It goes without saying that the features that are mentioned above and those still to be explained below can be used not only in the respectively specified combination but also in other combinations or on their own without departing from the scope of the present invention.

Further scope of applicability of the present invention will become apparent from the detailed description given hereinafter.

However, it should be understood that the detailed description and specific examples, while indicating preferred embodiments of the invention, are given by way of illustration only, since various changes. combinations and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figures 1A, 1B:
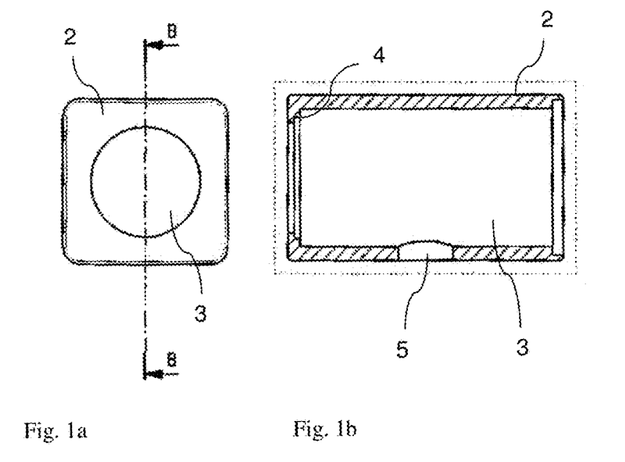
FIGS. 1a to 1c show a housing of the endoscope head of an exemplary embodiment of an endoscope according to the invention in an end view, a sectional view and an oblique view.

Represented in a simplified form in FIGS. 1a to 5c are components of an endoscope head that are designed for connecting according to an exemplary embodiment of the method according to the invention, and also the arrangement 1 of the components set up for the brazing process. FIG. 1a shows the housing 2 of the endoscope head in an end-on view. Represented in FIG. 1b is a longitudinal section of the housing 2 along the line B-B (see FIG. 1a). FIG. 1c shows the housing 2 in an oblique view. The housing 2 is of a substantially cuboidal design, or is designed in the form of a square column with beveled edges. The housing 2 has a substantially cylindrical bore 3, which passes right through in the longitudinal direction and the openings at both ends of which are formed in a stepped manner, an annular, likewise stepped stop 4 being provided in one of the openings. The side walls of the housing 2 are provided with transverse bores 5, 6.

Figure 1C:
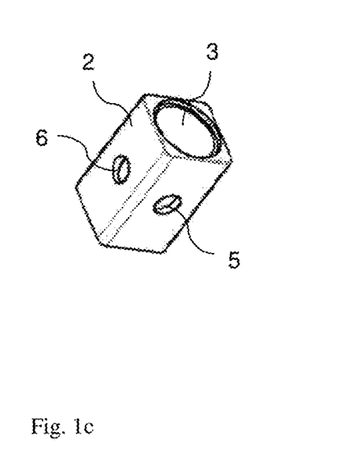
Figure 2A:
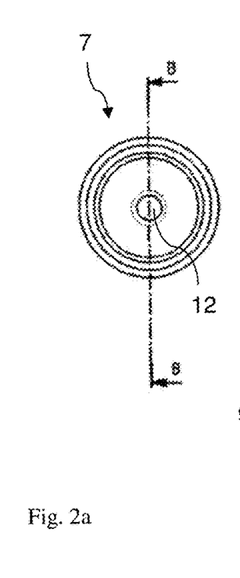
FIGS. 2a to 2c show a built-in part for the housing of FIGS. 1a to 1c in corresponding views, FIG. 2 showing an enlarged sectional view.
Figure 2B:
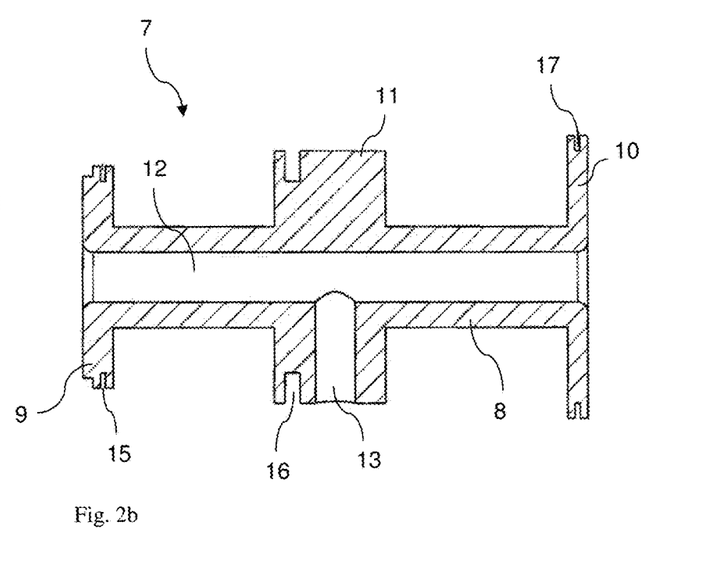
Figure 2C:
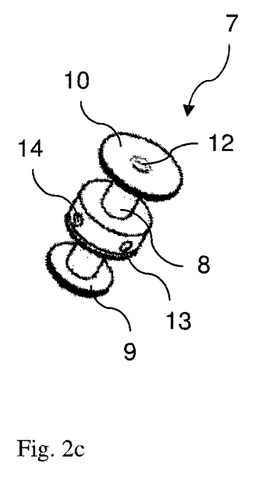

In FIGS. 2a to 2c, a built-in part that is designed as an inner bush 7 and is designed for inserting into the housing 2 shown in FIGS. 1a to 1c and for connecting to the latter by high-temperature brazing is represented in an end-on view, as a longitudinal section along the line B-B (see FIG. 2a) and in an oblique view. The inner bush 7 has a shank 8, which is cylindrical in certain portions and bears at each of its two ends a disk 9, 10 and in its middle part an enlarged cylinder 11. The inner bush 7 has a longitudinal through-bore 12. The cylinder 11 has two transverse bores 13, 14, which reach into the longitudinal bore 12. The disks 9, 10 and the cylinder 11 respectively have an incision, which is formed as a peripheral annular groove 15, 16, 17 and serves as a brazing solder reservoir. As shown in the enlarged representation of FIG. 2b, in comparison with FIGS. 2a and 2c, the annular grooves 15, 16, 17 respectively have a rectangular cross section. Correspondingly preformed brazing preforms may be introduced into the annular grooves 15, 16, 17.

Figure 3:
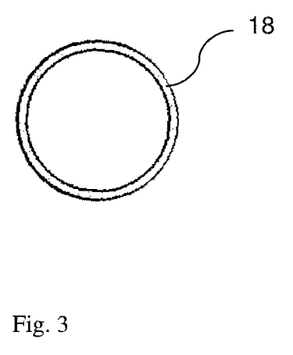
FIG. 3 shows a brazing preform for use with the built-in part according to FIGS. 2a to 2c in a plan view.

A brazing preform suitable for introducing into the annular grooves 15, 16, 17, designed as a brazing ring 18, is schematically represented in FIG. 3. The brazing ring 18 is produced by punching out from a brazing mat with a respectively suitable thickness, the thickness of the brazing mat corresponding approximately to the width of the respective annular groove 15, 16, 17, into which the brazing ring 18 is introduced. The width of the brazing ring 18 corresponds substantially to the depth of the respective annular groove 15, 16, 17. The brazing mat, and consequently the brazing ring 18, contains a high-temperature brazing solder in solid form, for instance as powder. In particular, the brazing mat may be produced powder-metallurgically with a nickel-based solder or iron-based solder and a binder. The brazing ring 18 may be deformable or else for instance be divided into ring segments, in order to facilitate the introduction into the annular grooves 15, 16, 17. The brazing ring 18 or the ring segments may be fixed in the annular grooves 15, 16, 17 with frictional or interlocking engagement or preferably by an adhesive introduced beforehand into the respective annular groove 15, 16, 17.

Figure 4A:
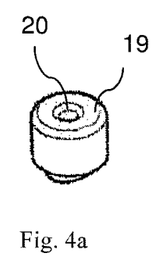
FIGS. 4a and 4b show a built-on part for the housing of FIGS. 1a to 1c in two views.
Figure 4B:
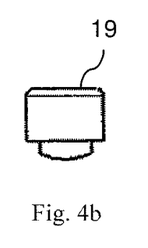

Also represented in two views in FIGS. 4a and 4b is a connecting part 19, which can be attached to the housing 2 of the endoscope head. The connecting part 19 may serve for example as a flushing connection or as a light connection and has for this purpose a through-bore 20.

Figure 5A:
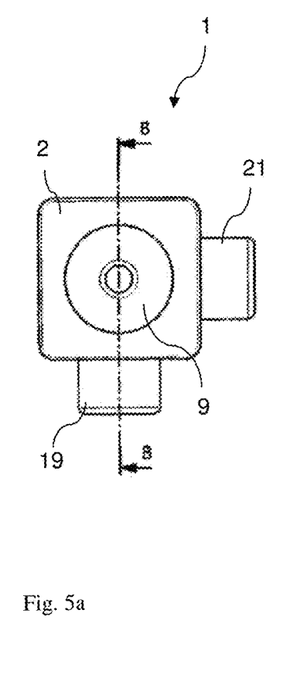
FIGS. 5a to 5c show an arrangement of the components of FIGS. 1a to 4b for the brazing process in an end view, a sectional view and an oblique view.
Figure 5B:
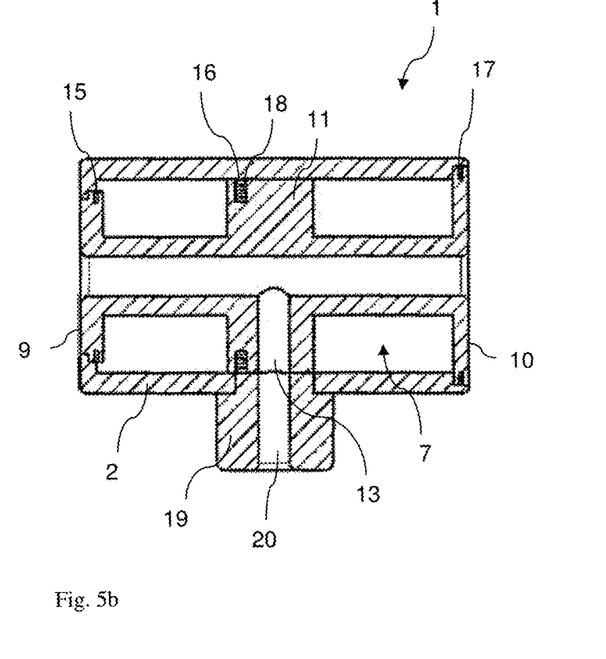
Figure 5C:
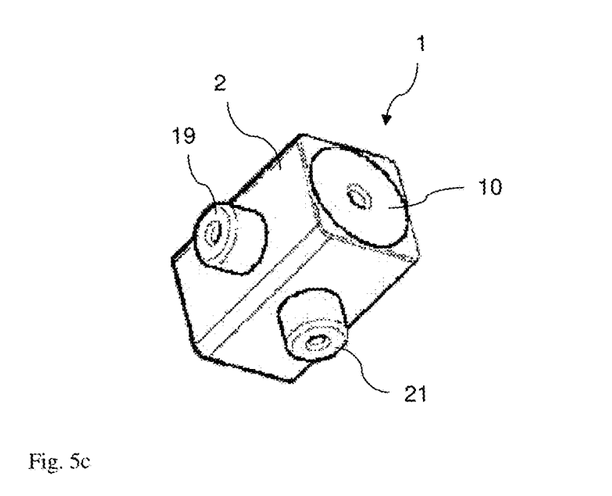

In FIGS. 5a to 5c, the arrangement 1 comprising the housing 2, the inner bush 7 and the connecting part 19 and also a further connecting part 21, including the inserted brazing preforms which have been put together for the brazing operation, are shown in an end-on view (FIG. 5a). FIG. 5b shows the arrangement 1 in a longitudinal section along the line B-B (see FIG. 5a), and FIG. 5c shows the arrangement 1 in an oblique view. As can be seen in particular in FIG. 5b in comparison with FIGS. 1b and 2b, the inner bush 7 has been inserted into the bore 3 of the housing 2 in such a way that the disk 9 of the inner bush 7 lies against the step of the stop 4. The two disks 9, 10 fill the respective openings of the bore 3 apart from peripheral brazing gaps formed between the outer circumference of the disk 9, 10 and the inner wall of the housing 2; similarly, a brazing gap is formed between the outer circumference of the cylinder 11 and the inner wall of the housing 2. The connecting parts 19, 21 have been inserted into the transverse bores 5, 6 of the housing 2 in such a way that the transverse bores 13, 14 of the inner bush 7 continue into corresponding inner bores 20 of the connecting parts 19, 21. As can be seen in particular in FIG. 5b, the brazing solder reservoirs formed by the annular grooves 15, 16, 17 are adjacent the brazing gaps between the inner bush 7 and the housing 2. Furthermore, the brazing solder reservoir formed by the annular groove 16 provided in the cylinder 11 is adjacent the joining locations between the connecting parts 19, 21, the cylinder 11 and the housing 2, where corresponding brazing gaps are likewise provided. In order to form brazing gaps suitable for high-temperature brazing, the housing 2 and/or the inner bush 7 may have projections, with which the inner bush 7 is held with frictional contact within the housing 2, or the inner bush 7 may be held in an appropriate position within the housing 2 by individual laser welding points (not represented in the figures); the same applies correspondingly to the connecting parts 19, 21.

In FIG. 5b, it is indicated that a respectively fitting brazing ring 18 has been inserted into the annular grooves 15, 16, 17. This ring is dimensioned to respectively fill the volume of the annular groove 15, 16, 17 and provide the amount of liquid brazing solder required for filling the respectively assigned brazing gap. For this purpose, the volume of the respective annular groove and the brazing ring 18 inserted therein may for example be greater by approximately 10% than that of the assigned brazing gap, in order to compensate for the loss of volume due to evaporation of the binder.

For connecting the housing 2, the inner bush 7 and the connecting parts 19, 21, a respectively fitting brazing ring 18 is inserted into the annular grooves 15, 16, 17. Then, the inner bush 7 fitted with the brazing rings 18 is inserted into the housing 2 and possibly held therein by further measures, for instance laser welding points. Furthermore, the connecting parts 19, 21 are inserted into the transverse bores 5, 6 of the housing 2 and possibly held therein by further measures. The components mentioned may form a subassembly. The arrangement 1 shown in FIGS. 5a to 5c, comprising the housing 2, the inner bush 7 with the brazing rings 18 and the connecting parts 19, 21, is then heated in a continuous furnace to a temperature that lies above the melting temperature of the high-temperature brazing solder contained in the brazing rings 18. The high-temperature brazing solder is preferably a nickel-based solder or an iron-based solder, and the brazing temperature to which the arrangement 1 is heated lies in the range between 1050 and 1200° C., the temperature being kept in this range for for example 10 to 15 minutes. The high-temperature brazing solder thereby liquefies and, on account of the capillary action, flows into the brazing gaps formed between the components to be connected to one another. During the subsequent cooling down, which may take place for example within one hour or within a few hours, the high-temperature brazing solder solidifies in the brazing gaps and thereby creates a solid, durable and seal-tight connection between the components to be connected to one another. The assembly produced is provided with further components in further steps of producing the endoscope.

Figure 6:
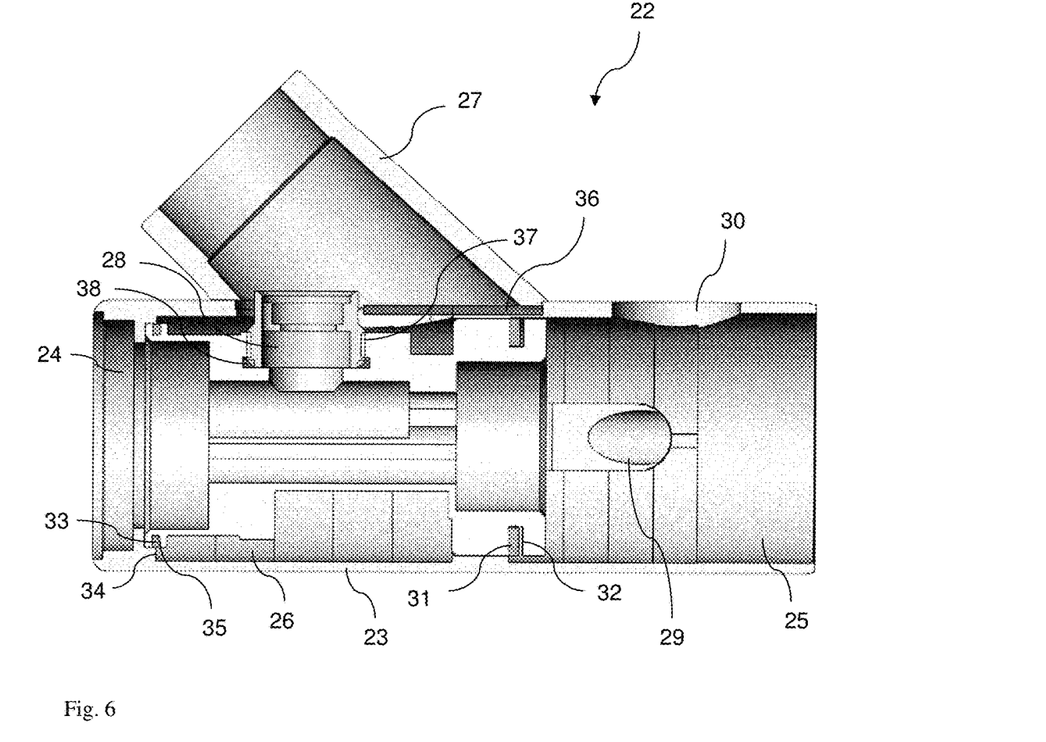
FIG. 6 shows an arrangement for the high-temperature brazing of components for the head of an endoscope according to a further exemplary embodiment of the invention in a longitudinal section.

In FIG. 6, an arrangement 22 comprising components for an endoscope head according to a further exemplary embodiment of the invention is represented in a partly sectioned sectional view. The endoscope head has an approximately cuboidal housing 23 with a longitudinal bore that is cylindrical in certain portions and into which an inner bush 24 and further built-in parts 25, 26 can be inserted. Attached obliquely onto the housing 23 is a light connection with a light connecting sleeve 27. An intermediate piece 28 is arranged between the light connection and the inner bush 24. Also provided are openings 29, 30, into which further built-on parts, for example flushing and suction connections, can be inserted. The inner bush 24 is designed for receiving an optical tube and a lightguide channel of the endoscope and the intermediate piece 28 is designed for guiding optical fibers.

Furthermore, in FIG. 6 a number of joining locations are represented by way of example, with the associated brazing solder reservoirs or the brazing preforms inserted therein. For providing the high-temperature brazing solder for a brazing gap, which is formed between the built-in part 25 and the inner side of the housing 23, a first brazing ring 31 is inserted in a brazing solder reservoir formed by an annular collar 32 and fixed there by adhesion. For bounding the brazing solder reservoir, the annular collar 32 has a wall extending transversely in relation to the longitudinal direction, as a termination on one side in the longitudinal direction, and a wall perpendicular thereto as a connection on the inner side. The brazing ring 31 may be inserted into the brazing solder reservoir in the longitudinal direction. For connecting the further built-in part 26 to the housing 23, a second brazing ring 33 is attached to the inner side of the housing 23 and the built-in part 26 in a region in which the built-in part 26 butts against a step 34 of the housing 23, and is fastened there by adhesive; the brazing solder reservoir is likewise bounded here by an annular collar 35. For providing the brazing solder for filling a brazing gap between the light connecting sleeve 27 and an outer side of the housing 23, a brazing solder reservoir filled with an elliptical brazing ring 36 is provided between the housing 23 and the light connecting sleeve 27. The intermediate piece 28 is connected to the housing 23 by way of a joining location that is formed between the outer wall of the intermediate piece 28 and a transverse sleeve 37 of the housing 23, for which a brazing ring 38 is likewise provided in a corresponding brazing solder reservoir.

The brazing gaps of the joining locations typically have a width of one or several tenths of a millimeter, a height of approximately one or several millimeters and a length in the range of millimeters or centimeters, so that a required volume of the high-temperature brazing solder of several $mm^3$ is obtained. The brazing solder reservoirs and the brazing rings 31, 33, 36, 38 inserted into them are dimensioned correspondingly to provide the appropriate amount of high-temperature brazing solder. In particular, the volume of the brazing solder reservoir and of the respective brazing ring 31, 33, 36, 38 is approximately 10% greater than the required volume of the high-temperature brazing solder, in order to compensate for the evaporation of the binder. Furthermore, the brazing ring 36 in particular may additionally be made to greater dimensions, in order to make an additional brazing solder volume available for the formation of a fillet seam.

The arrangement 22 shown in FIG. 6 may be heated as a whole in a furnace, for instance a continuous furnace, to a brazing temperature. The in the brazing rings 31, 33, 36, 38 and possibly further brazing preforms not represented in FIG. 6, which are assigned to further joining locations, liquefies and flows into the brazing gaps of the corresponding joining locations. As a result, a plurality of components can be connected to one another with a plurality of joining locations in a single operation, irrespective of the accessibility of the joining location. As a result, a considerable simplification of the production process can be achieved. In further production steps, further components, for instance an optical tube, an eyepiece cup, light guides and also the shank of the endoscope, are inserted into the assembly created or are attached to it (not represented).

For the sake of overall clarity, not all of the designations are represented in all of the figures. Designations that are not explained in relation to one figure have the same meaning as in the other figures.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. Method for connecting at least two components of an endoscope or medical instrument, the method comprising:
   introducing at least one brazing preform, which contains a high-temperature brazing solder, into at least one brazing solder reservoir of at least one of the components,
   arranging the at least two components so that the at least two components are held in relation to one another in such a way that at least one brazing gap, that is in capillary connection with the at least one brazing solder reservoir, is formed between joining regions of the at least two components that are assigned to one another, the at least one brazing solder reservoir and the at least one brazing gap being formed such that a volume of the at least one brazing solder reservoir is greater than a volume of the brazing gap by at least an amount that corresponds to a proportion of a binder in the at least one brazing preform, and
   heating the at least two components and the at least one brazing preform to a brazing temperature of the high-temperature brazing solder.

2. The method according to claim 1, wherein, for forming the at least one brazing gap, the at least two components are held against one another with interlocking, frictional or material-bonding engagement.

3. The method according to claim 1, wherein the at least two components have a plurality of joining locations that are formed by joining regions assigned to one another and to which at least one brazing solder reservoir is respectively assigned.

4. The method according to claim 1, wherein more than two components are connected to one another, at least two joining locations that are formed by joining regions assigned to one another being provided.

5. The method according to claim 1, wherein the high-temperature brazing solder is a nickel-based solder or an iron-based solder.

6. The method according to claim 1, wherein the brazing preform is produced from a brazing mat.

7. The method according to claim 1, wherein the at least one brazing preform introduced into the at least one brazing solder reservoir is fixed in the at least one brazing solder reservoir.

8. The method according to claim 7, wherein the at least one brazing preform introduced into the at least one brazing solder reservoir is fixed in the at least one brazing solder reservoir by adhesion or with interlocking engagement.

9. The method according to claim 1, wherein the at least one brazing solder reservoir and the at least one brazing preform are at least dimensioned in such a way that the brazing solder reservoir is substantially filled by the brazing preform when the brazing preform is introduced into the at least one brazing solder reservoir and, during the heating, the brazing gap is substantially filled completely with brazing solder.

10. The method according to claim 1, wherein the at least one brazing solder reservoir includes at least a first brazing solder reservoir and a second brazing solder reservoir, wherein one of the at least two components is a shank having a first disk flange provided at a proximal end thereof and a second disk flange provided at a distal end thereof, the first disk flange having an annular groove extending around an outer periphery thereof, the annular groove of the first disk flange forming the first brazing solder reservoir and the second disk flange having an annular groove extending around an outer periphery thereof, the annular groove of the second disk flange forming the second brazing solder reservoir, wherein the at least one brazing preform includes at least a first brazing preform and a second brazing preform, wherein the introducing of the at least one brazing preform includes introducing the first brazing preform into the first brazing solder reservoir of the first disk flange and introducing the second brazing preform into the second brazing solder reservoir, wherein another one of the at least two components is a hollow housing, and wherein the arranging of the at least two components includes sliding the shank inside the hollow housing after introducing the first brazing preform and the second brazing preform.

* * * * *